United States Patent [19]
Cadet et al.

[11] Patent Number: 5,948,967
[45] Date of Patent: Sep. 7, 1999

[54] ACOUSTIC ANALYSIS OF GAS MIXTURES

[75] Inventors: Gardy Cadet, Orange, N.J.; Fred Paul Partus, Atlanta, Ga.

[73] Assignee: Lucent Technologies, Inc., Murray Hill, N.J.

[21] Appl. No.: 08/998,440

[22] Filed: Dec. 26, 1997

[51] Int. Cl.⁶ .................................................. G01N 29/02
[52] U.S. Cl. ........................................ 73/24.01; 73/24.06
[58] Field of Search ................................ 73/24.01, 24.06, 73/61.49, 61.75, 61.79, 64.53, 64.56, 863.61

[56] References Cited

U.S. PATENT DOCUMENTS

| 5,501,098 | 3/1996 | Cadet et al. | 73/24.01 |
| 5,625,140 | 4/1997 | Cadet et al. | 73/24.01 |

FOREIGN PATENT DOCUMENTS

| 1335447 | 7/1963 | France | 73/24.01 |
| 798323 | 7/1958 | United Kingdom | 73/24.01 |
| 801757 | 9/1958 | United Kingdom | 73/24.01 |

OTHER PUBLICATIONS

Kniazuk et al. "Ultrasonic Gas Analyzer", Instruments & Automation, vol. 28, Nov. 1995, pp. 1916–1917.

Primary Examiner—Daniel S. Larkin

[57] ABSTRACT

An apparatus is provided comprising means for creating substantially the same or mirror image first and a second gas flow patterns near the surface of first and second transducers. The means include an inlet conduit, an inlet port, a main conduit device, and an output port. A device is also provided for causing the first transducer to send a signal to the second transducer and for measuring the time taken for the signal to travel from first transducer to the second transducer. The inlet port is coupled to the inlet conduit, preferably centrally, and the output port is coupled to the main conduit device. The inlet conduit is comprised of a first branch and a second branch. Both branches have first and second ends, the second end of the first branch being coupled to the main conduit device at a first location, and the second end of the second branch being coupled to the main conduit device at a second location. Gas preferably flows into the inlet port, part of the gas goes into the first branch and part of the gas goes into the second branch. The main conduit device is preferably comprised of a first flange, a second flange, and a main conduit. The main conduit preferably has first and second ends.

13 Claims, 5 Drawing Sheets

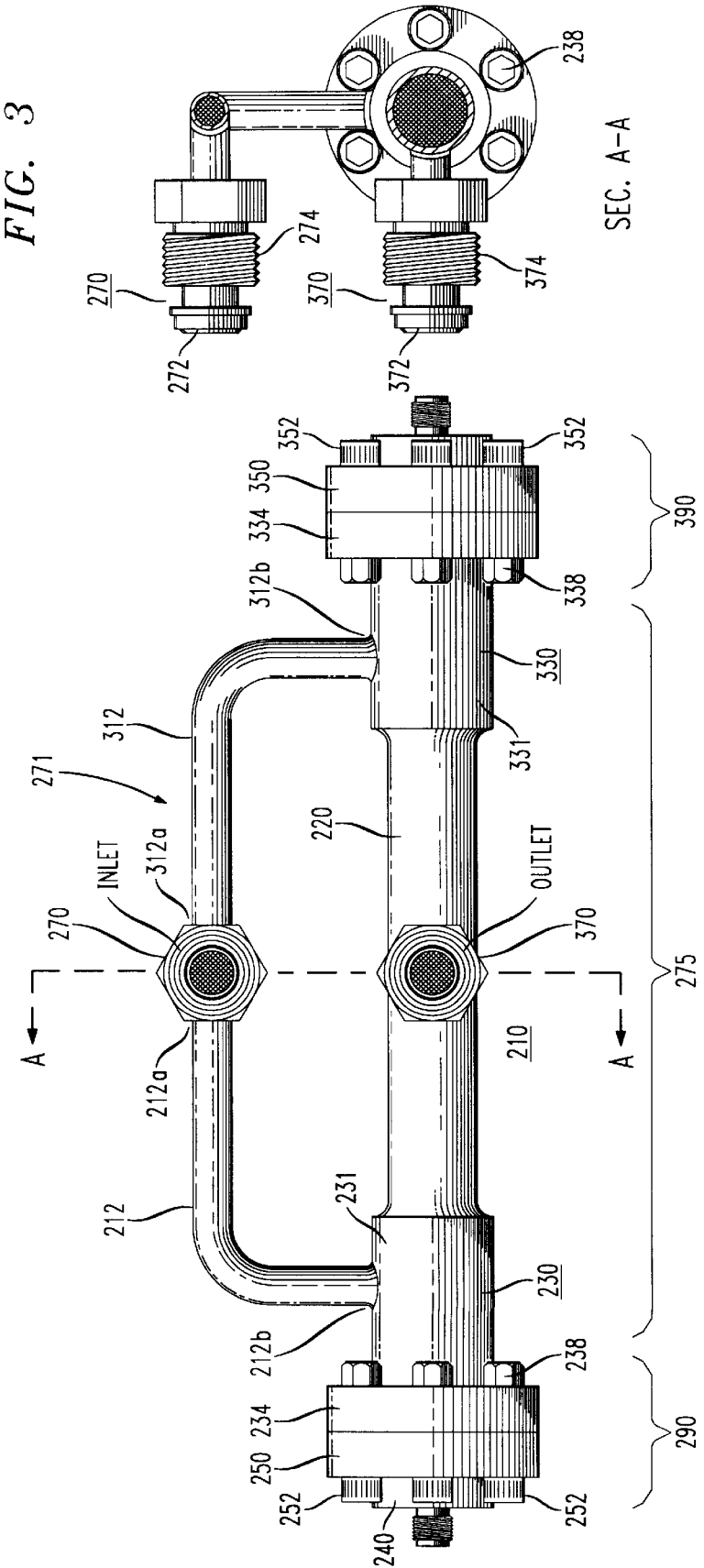

ACOUSTIC ANALYSIS OF GAS MIXTURES

FIELD OF THE INVENTION

The invention relates to the field of acoustic gas monitoring and, more particularly, to the in-line monitoring and control of the composition of gas mixtures.

BACKGROUND OF THE INVENTION

U.S. Pat. No. 5,501,098 to Cadet et al., incorporated by reference herein, discloses an acoustic gas composition analysis cell 10 which is comprised of first and second transducer housings 40 for sealing first and second ends respectively of a conduit 20. Each transducer housing 40 includes a transducer 80. One of the ports 70 act as an input port for gas flow and one of the ports 70 act as an outlet port for gas flow. Thus, one of the transducers 80 is located upstream of the gas flow and one located downstream. Because of the doppler shift effect, a measurement of the time of travel of an acoustic signal from one transducer 80 to another, is affected by whether the acoustic signal starts from a downstream transducer and then is transmitted to an upstream transducer or starts from an upstream transducer and then is transmitted to a downstream transducer. I.e., the time of travel measurement is affected by whether the signal is travelling in the direction of the flow of the gas or against the flow of the gas.

U.S. Pat. No. 5,625,140 to Cadet et al., incorporated by reference herein, discloses a gas composition anaylsis cell 10 wherein a sound absorbing sleeve 100 is wrapped around a conduit 20 to reduce noise.

As described in U.S. Pat. No. 5,501,098 to Cadet et. al., incorporated by reference herein, in many manufacturing operations accurate information concerning a gas composition is necessary to control a particular process. (Cadet, 5,501,098, col. 1, lns. 14–30). In line gas monitoring is often used to ensure a consistent delivery of gas. Acoustic analysis can be used to determine the concentration of a component of a gas mixture. The transit time or time of travel of sonic pulses between transducers is measured and used to determine the velocity of sound in the gas. From the velocity, the composition of a binary mixture of gas can be determined. For more details refer to col. 1, ln. 30–col. 3, ln. 4, in Cadet et. al., 5,501,098, which section is incorporated by reference herein.

SUMMARY OF THE INVENTION

The present invention in at least one embodiment provides a method and apparatus for creating uniform or mirror like gas flow patterns near a transmitting transducer and a receiving transducer. The uniform or mirror like gas flow patterns preferably reduce or eliminate the doppler effect on acoustic signal transit time measurements. Because of the gas flow patterns, strictly speaking, there is no downstream or upstream transducer.

The present invention in one embodiment provides an apparatus comprised of an inlet conduit, an inlet port coupled to the inlet conduit, a main conduit device, and an output port coupled to the main conduit device. The inlet conduit is preferably comprised of a first branch and a second branch. Both branches have first and second ends, the second end of the first branch being coupled to the main conduit device at a first location, and the second end of the second branch being coupled to the main conduit device at a second location. The first ends of the first and second branches are preferably coupled together. Gas preferably flows into the inlet port, part of the gas goes into the first branch and part of the gas goes into the second branch.

Preferably, the inlet port is coupled substantially in the center of the inlet conduit. The main conduit device is preferably comprised of a first flange, a second flange, and a main conduit. The main conduit, preferably, has first and second ends. The first flange, preferably, is connected to the main conduit at the main conduit's first end, the second flange, preferably, is connected to the main conduit at the main conduit's second end. The second end of the first branch is preferably coupled to the first flange and the second end of the second branch is coupled to the second flange. The first flange is connected to a first transducer device comprised of a first transducer, and the second flange is connected to a second transducer device, comprised of a second transducer. The first and second transducer devices, preferably, seal off the first and second ends of the main conduit.

The first and second branches of the inlet conduit, in one embodiment, together form a U-shape. The first ends of the first and second branches are preferably seamlessly connected together as an integrated member.

In one embodiment of the present invention, first and second transducers are provided, each one having a surface. Means are also provided for creating a first and a second gas flow pattern near the surface of the first and second transducers. The means may be comprised of the inlet conduit, inlet port, main conduit device, and an output port, all as previously described. A device for causing the first transducer to send a signal to the second transducer and for measuring the time taken for the signal to travel from first transducer to the second transducer is also provided. Preferably, the first gas flow pattern and the second gas flow patterns are substantially the same or are mirror images of one another.

BRIEF DESCRIPTION OF THE DRAWINGS

FIG. 2 shows a side view of a gas composition analysis cell in accordance with an embodiment of the present invention;

FIG. 3 shows a front view of a gas composition analysis cell including an inlet conduit;

DETAILED DESCRIPTION OF THE DRAWINGS

Figure 1:
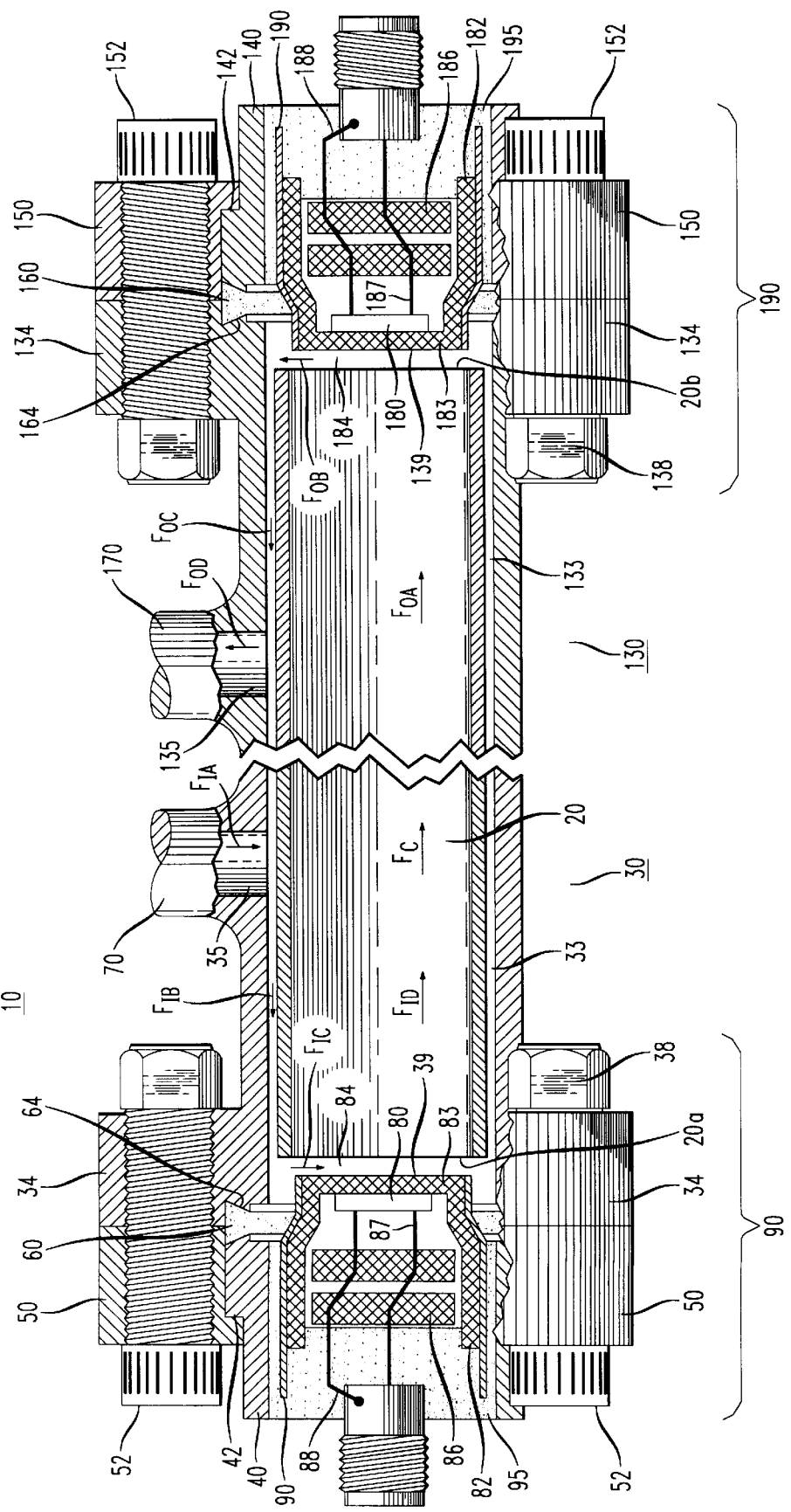
FIG. 1 shows a diagram of gas flow through a prior art gas composition analysis cell.

FIG. 1 shows a diagram of gas flow through a prior art gas composition analysis cell 10, of the type found in U.S. Pat. No. 5,501,098, to Cadet et al., which is incorporated by reference herein. The cell 10 is comprised of first transducer device 90 which is coupled to a conduit 20 by flange member 30 and a second transducer device 190 which is coupled to the conduit 20 by flange member 130. The first and second transducer devices 90 and 190 are comprised of first and second transducers 80 and 180, and first and second transducer housings 40 and 140, respectively. The first transducer 80 has a metal housing 82 surrounding it which has a surface 83 facing the first end 20a of the conduit 20 and the second transducer 180 has a metal housing 182 surrounding it which has a surface 183 facing the second end 20b of the conduit 20. Cylindrical gap 39 is located between the transducer housing surface 83 and the conduit 20 first end 20a and cylindrical gap 139 is located between the transducer housing surface 183 and the conduit 20 second end 20b.

In the prior art cell 10, gas comes in through an inlet port 70 and flows into the space 33. The gas flows roughly in the direction shown by the vector $F_{IA}$, downward into the space 33. The gas then flows to the left through the space 33, as shown by the vector $F_{IB}$. The gas then flows across the transducer housing surface 83, in the direction of vector $F_{IC}$, and finally outwards and perpendicularly to the surface 83 of the transducer housing 82 and to the surface of the transducer 80, in the direction $F_{ID}$. The gas then flows through the conduit 20 in the direction $F_C$, towards the other end 20b of the conduit 20.

The gas flows towards the surface of the transducer housing 183 and thus the surface of transducer 180, in the direction of the vector $F_{OA}$. The gas then flows across the surface of the transducer housing surface 183 in the direction of the vector $F_{OB}$. The gas then flows in the space 133 in the direction of vector $F_{OC}$, and finally into the outlet port 170 in the direction of vector $F_{OD}$.

The gas flow pattern near the surface of the transducer housing surface 83, comprised of $F_{IA-D}$, can be summarized as follows: the gas flows across the surface of the transducer housing surface 83 and then flows away from the transducer housing surface 183 into the conduit 20. Because the gas flows away from the transducer 80 into the conduit 20, the transducer 80 can be thought of as an upstream transducer.

The gas flow pattern near the transducer housing surface 183, copmrised of vectors $F_{OA-D}$, can be summarized as the gas flows from the conduit 20, towards the surface of the transducer housing 183, across the transducer housing surface 183 and then into the narrow space 133. Because the gas from the conduit 20 flows towards the surface of the transducer 180, the transducer 180 can be thought of as a downstream transducer.

When the upstream transducer 80 sends an acoustic signal through the conduit 20 to the downstream 180 transducer, the time of travel of the acoustic signal is affected by the flow rate of the gas, due to the doppler effect. Likewise, when the downstream transducer 180 sends an acoustic signal through the conduit 20 to the upstream 80 transducer, the time of travel of the acoustic signal is affected by the flow rate of the gas, due to the doppler effect. There will be a difference between the measured time of travel for the acoustic signal depending on whether the signal is travelling upstream or downstream.

Table A shows a table of experimental results for time of travel of an acoustic signal in the upstream and in the downstream direction for various flow rates of a gas. The first column shows various flow rates of the gas in Standard Cubic Centimeters Per Minute (hereinafter "SCCM"). The second columns shows the various corresponding measured times of travel, in microseconds of an acoustic signal of 200 kilohertz which has travelled upstream, T(Up), i.e. from transducer 180 to the transducer 80. The third column shows the various corresponding measured times of travel, in microseconds of an acoustic signal of 200 kilohertz which has travelled downstream, T(Dn), i.e. from transducer 80 to the transducer 180. The fourth column shows the difference between the T(Up) and T(Dn), which is Delta-t, in microseconds.

In the first data row, for a flow rate of 200 SCCM, there is a difference in time of travel between the upstream and downstream directions, of 0.08 microseconds. The difference in time of travel of the acoustic signal (Delta-t) increases as the flow rate increases due to increase in doppler shift. For a flow rate of 3000 SCCM, the difference in time of travel is 0.97 microseconds.

TABLE A

Upstream and Downstream Transducers

| Flow Rate ($O_2$ used) rate in SCCM | Time of travel Upstream (TUp) (microseconds) | Time of Travel Downstream (TDn) (microseconds) | Delta-t (microseconds) |
| --- | --- | --- | --- |
| 200 | 346.07 | 346.15 | 0.08 |
| 500 | 346.23 | 346.01 | 0.22 |
| 1000 | 346.34 | 345.9 | 0.44 |
| 1500 | 346.48 | 345.81 | 0.67 |
| 2000 | 346.56 | 345.72 | 0.84 |
| 3000 | 346.64 | 345.67 | 0.97 |

Figure 4:
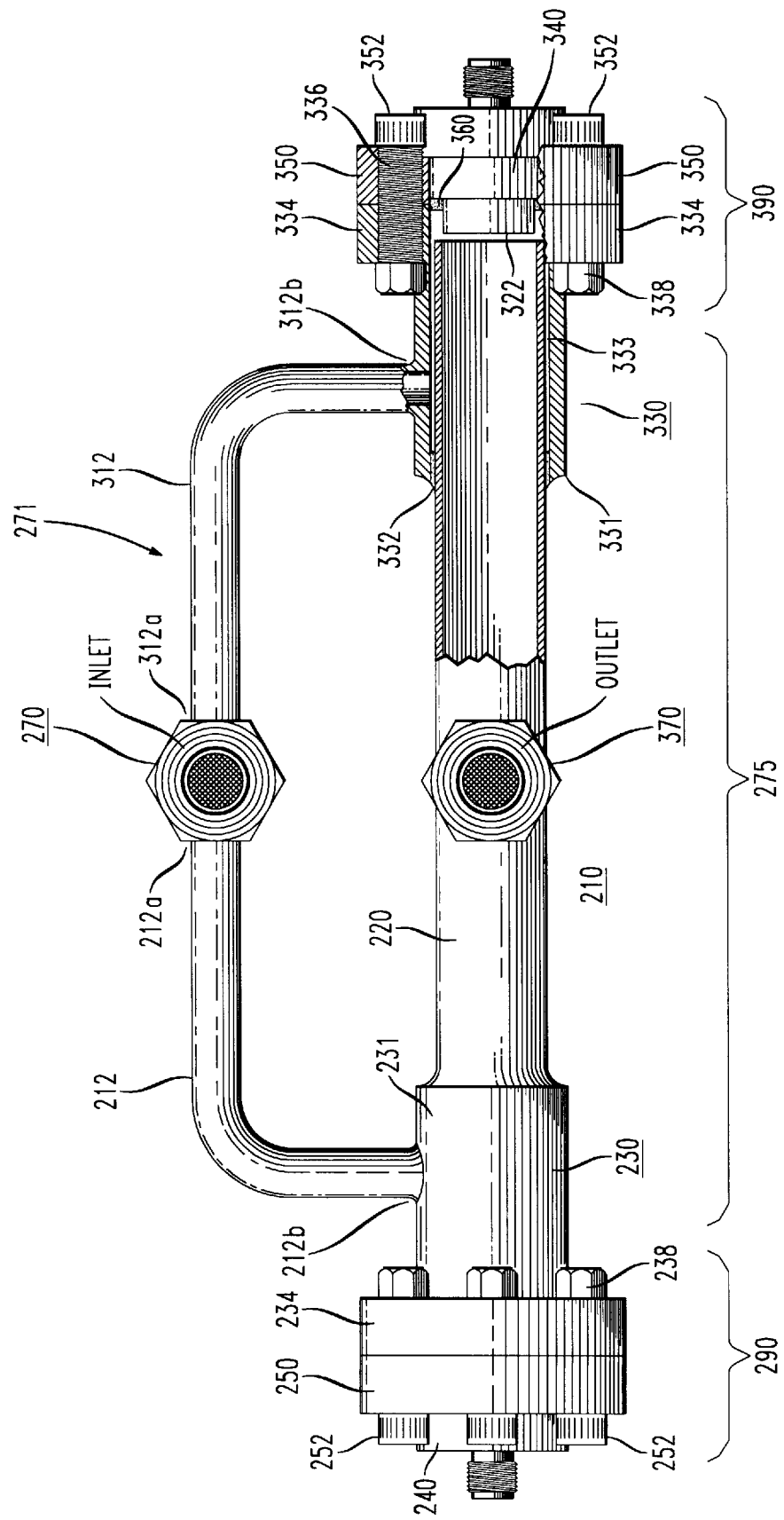
FIG. 4 is a side view in partial cross section of an acoustic gas analysis cell in accordance with the present invention.
Figure 5:
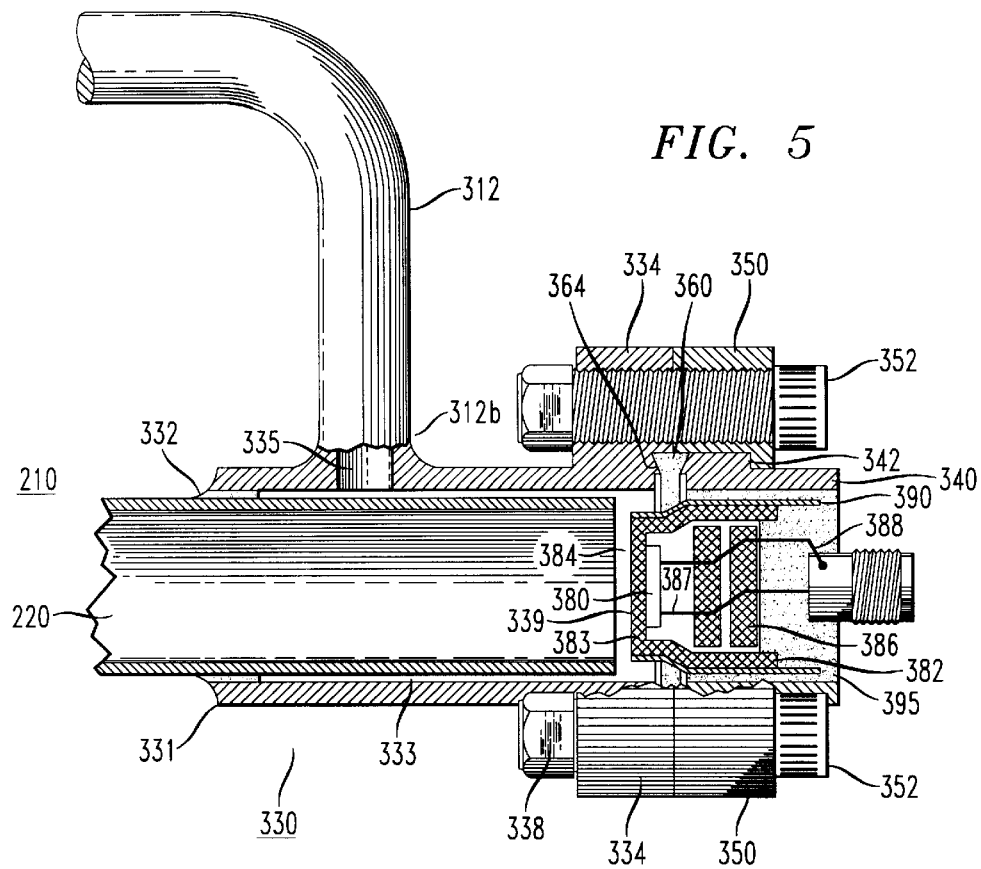
FIG. 5 is an enlarged view in partial cross section of a transducer and housing assembled in the acoustic gas analysis cell of the present invention.

FIGS. 2–5 show various views of a gas composition analysis 210 in accordance with an embodiment of the present invention. The gas composition analysis cell 210 includes many of the same components shown in composition analysis cell 10 of FIG. 1. For example, flange 30 and 130 of FIG. 1 correspond to Flanges 230 and 330 respectively of FIG. 2. Transducer devices 291 and 391 in FIGS. 2 and 4 correspond to transducer devices 90 and 190 in FIG. 1. FIG. 3 shows a front view of gas composition analysis cell 210 including an inlet U-shaped conduit 271. FIG. 4 is a side view in partial cross section of an acoustic gas analysis cell 210 in accordance with the present invention. FIG. 5 is an enlarged view in partial cross section of a transducer housing 340 assembled in the acoustic gas analysis cell 210 of the present invention. The following components shown in FIG. 5 are similar to the similarly numbered components shown in FIG. 4 of U.S. Pat. No. 5,625,140 and 5,501,098 to Cadet et. al., both of which are incorporated by reference herein. Weld 332, cylindrical portion 331, flange rim 334, through holes 336, mating flange 350, housing lip 342, fasteners 352, holes 356, nuts 338, gaskets 360, knife edges 364, sleeves 390, acoustic isolation material 382, impedance matching material 383, thin layer 384, space 385, backing material 386, transducer leads 387 and 388, and fixing agent 395 correspond to similarly numbered components in the aforementioned patents. Similar components for the side with the other transducer housing 240 are numbered in the 200s and have the same purpose and function. Outlet port 370 is shown in FIGS. 2–4. Mating members 272 and 372 and threaded fasteners 274 and 374 are shown in FIG. 3;

The gas composition cell 210 differs from the prior art device of FIG. 1 in the manner in which gas flows, enters, and exits the gas composition analysis cell 210.

FIGS. 2–5 and 7 show a U-shaped inlet conduit 271 comprised of a first branch 212 and second branch 312. The first branch 212 includes a first end 212a and a second end 212b, and the second branch 312 includes a first end 312a and a second end 312b. The U-shaped inlet conduit 271 is coupled to a main conduit device 275 which is comprised of main conduit 220 and flanges 230 and 330. The first branch 212 is connected at its second end 212b to the flange 230 and the second branch 312 is connected at its second end 312b to the flange 330.

Figure 7:
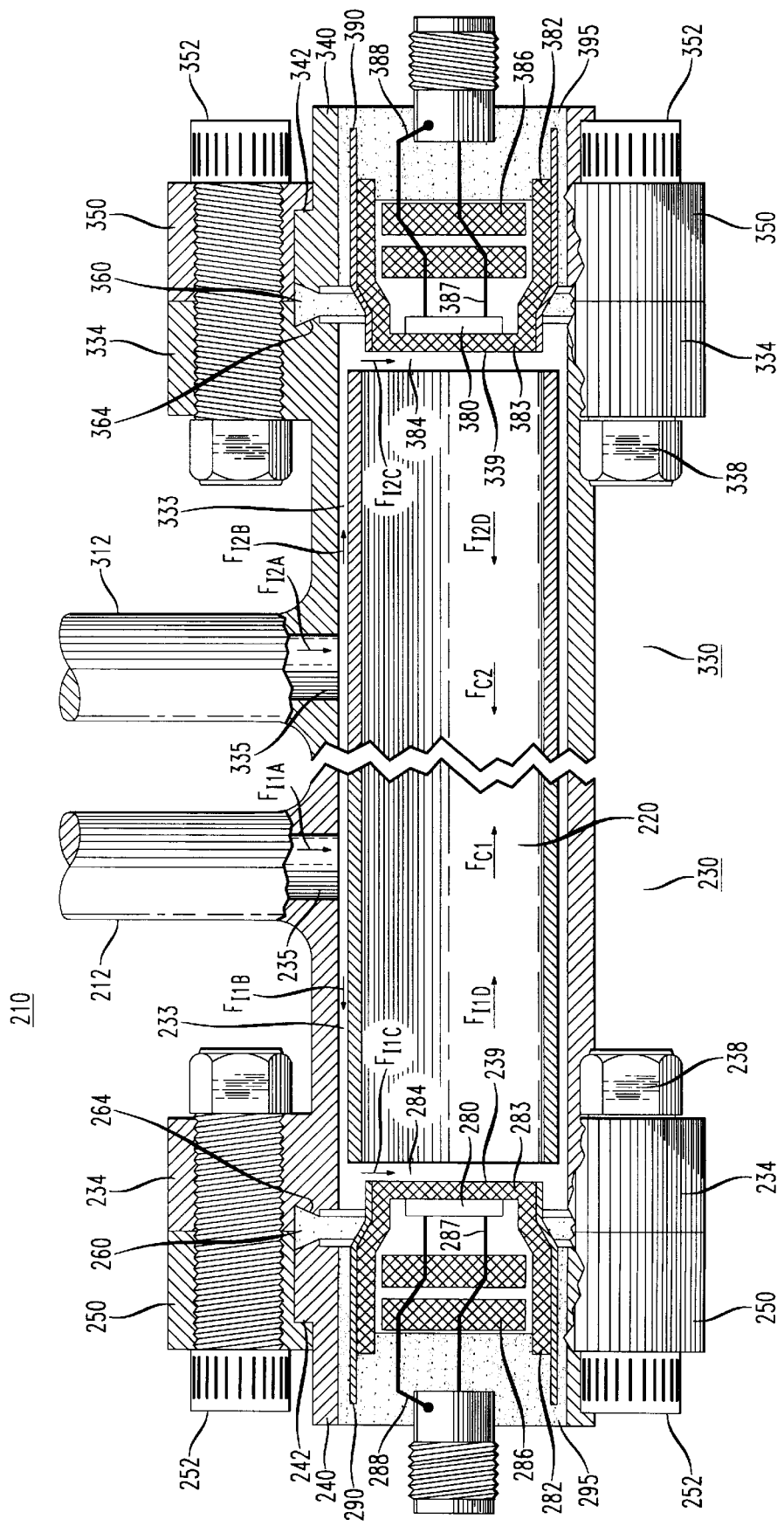
FIG. 7 shows a diagram of gas flow through the gas composition analysis cell of FIG. 2.

The second branch 312 is connected to the flange 330 through an aperture 335 so that gas flowing from the second branch 312 of the inlet conduit 271, can flow into the space 333 between the flange 330 and the main conduit 220, as shown in FIGS. 5 and 7. The first branch 212 is connected in the same manner to the flange 230 through an aperture 235, as shown in FIG. 7.

Referring to FIG. 7, the operation of one embodiment of the present invention will be described. Gas flows into the inlet port 270, and thus into the inlet conduit 271. Part of the gas, approximately fifty percent, flows into the first branch 212 and the remaining gas flows into the second branch 312. The gas flow into the first branch 212 proceeds into the space 233, in the direction of vector $F_{f1A}$. Afterwards the gas flow proceeds to the left in the space 233, in the direction of vector $F_{f1B}$. Then the gas flows continues across the surface of the transducer housing 283 in the direction of the vector $F_{f1C}$ and then finally away from the transducer 280 in the direction $F_{f1D}$. The gas from the first branch 212 then proceeds through the main conduit 220 as shown by vector $F_{C1}$.

The second portion of the gas from the input port 270, proceeds through the second branch 312 of the inlet conduit 271, and past the transducer housing surface 383 in a mirror image manner when compared with the gas flow through the first branch 212 past the transducer housing surface 283. The gas flows down from the second branch 312 and into the space 333, in the direction of the vector, $F_{f2A}$. Then the gas proceeds to the right and through space 333, in the direction of vector $F_{f2B}$, which is the mirror image of the left flow for the gas in space 233. The gas then proceeds downwards and across the surface of the transducer housing 383, in the direction of vector $F_{f2C}$, and finally outwards from the surface of the transducer housing 383 in the direction of the vector $F_{f2D}$. The gas from the second branch 312 then proceeds through the main conduit 220 as shown by vector $F_{C2}$.

The gas flow pattern shown roughly by vectors $F_{f1A-D}$ and the gas flow pattern shown roughly by vectors $F_{f2A-D}$ can be thought of as first and second gas flow patterns respectively. In the embodiment illustrated by FIG. 7, the first and second flow patterns are mirror images. From the perspective of looking out from the surface of the transducer 280 or 380 into the conduit 220, the first and second flow patterns are substantially similar. Gas comes towards transducer 80 from a narrow passage, i.e. space 233, the gas goes down and across the transducer 280 surface, and then the gas moves away, perpendicularly from the transducer 280 surface into a relatively wide main conduit 220. Similarly gas comes towards transducer 380 from a narrow passage, i.e. space 333, the gas goes down and across the transducer 380 surface, and then the gas moves away, perpendicularly from the transducer 380 surface into a relatively wide main conduit 220.

Because, transducer 280 and 380 experience substantially similar gas flow patterns, neither one is an upstream or a downstream transducer. Because of the similar flow patterns, the doppler effect is virtually eliminated. The time it takes for a particular acoustic signal to travel from transducer 280 to transducer 380 will be substantially the same as the time it takes for the same acoustic signal to travel from transducer 380 to transducer 280. Test data shown in table B shows virtually no difference between measurements. In table B, column one, shows various flows rates, column two shows corresponding time of travel of the acoustic signal from transducer 380 to transducer 280 ($T_{380-280}$), column three shows corresponding time of travel from transducer 280 to transducer 380 ($T_{280-380}$), and column four shows the difference in the time of travel measurements, (Delta-t).

TABLE B

DATA FOR EMBODIMENT OF PRESENT INVENTION

| Flow Rate (O2 used) rate in SCCM | Time of travel Trans$_{380}$ to Trans$_{280}$ (microseconds) | Time of Travel Trans$_{280}$ to Trans$_{380}$ (microseconds) | Delta-t (microseconds) |
|---|---|---|---|
| 200 | 520.43 | 520.42 | 0.007 |
| 500 | 520.43 | 520.41 | 0.014 |
| 1000 | 540.44 | 520.42 | 0.016 |
| 1500 | 520.44 | 520.43 | 0.008 |
| 2000 | 520.44 | 520.44 | 0.002 |
| 3000 | 520.44 | 520.4 | 0.004 |

Figure 6:
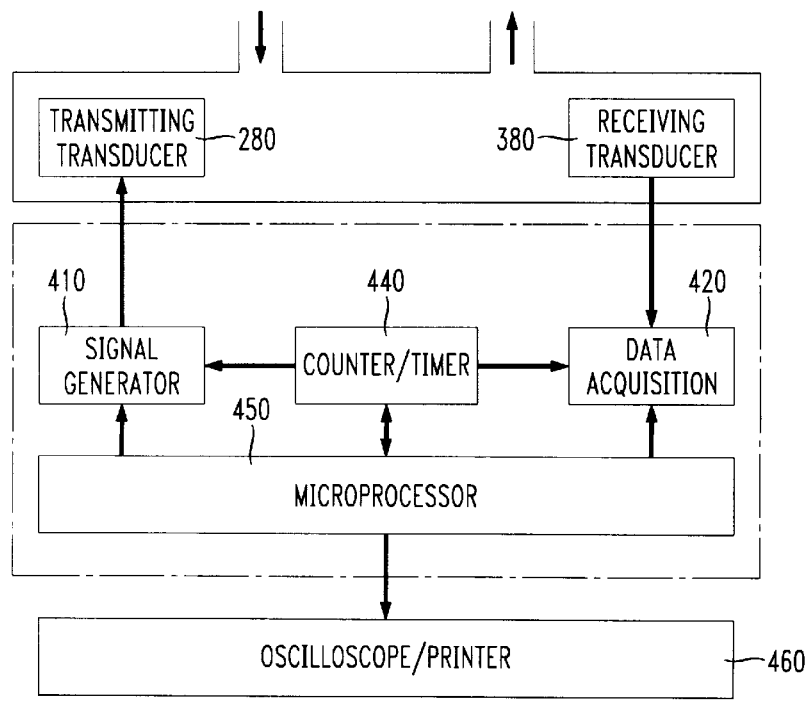
FIG. 6 is a schematic block diagram of the signal generating and data processing circuit used with the acoustic gas analysis cell of FIG. 2.

Because there is no difference in the time of travel of the acoustic signal regardless of direction, one transducer can be a dedicated transmitter and one can be a dedicated receiver. FIG. 6 is a schematic block diagram of the signal generating and data processing circuitry used with the acoustic gas analysis cell of FIG. 2. FIG. 6 shows transducer 280 as a dedicated transmitting transducer, and transducer 380 as a dedicated receiving transducer. Signal generator 410, counter/timer 440, data acquisition block 420, microprocessor 450 and oscilloscope/printer 460, can function as the similarly numbered components described in FIG. 5 of the previous Cadet U.S. patents, such as 5,501,098. However, note that a transmitter/receiver switch such as switch 130 shown in FIG. 5 of Cadet, 5,501,098 can be eliminated since the transducers 280 and 380 are dedicated as a transmitter and a receiver, respectively.

The present invention in one embodiment eliminates the need for sending one acoustic signal from a first transducer to a second transducer and then a second acoustic signal, of the same type, back from the second transducer to the first transducer. Previously, such upstream and downstream signals were needed to average out the doppler effect. The elimination of the back and forth signals means that one transducer can be a dedicated transmitter while the other can be a dedicated receiver, thus eliminating the need for the transmitter/receiver switch 230 previously shown in FIG. 5 of U.S. Pat. No. 5,625,140 to Cadet incorporated herein by reference. This also means faster analysis, since less signals are needed and less computer software or hardware computation time since averaging of signal values is not needed.

The present invention in one embodiment is particularly suitable for systems where the time of travel or flight measurement of the acoustic signal is used to determine the concentration of a gas component.

We claim:

1. An apparatus comprised of:
   a first transducer device;
   a second transducer device;
   an inlet conduit comprised of:
      a first branch having first and second ends, the second end coupled to a main conduit device at a first location;
      a second branch having first and second ends, the second end coupled to the main conduit device at a second location, and the first end of the second branch being connected to the first end of the first branch;
   an inlet port coupled to the inlet conduit;
   an output port coupled to the main conduit device at a third location;

wherein the first, second, and third locations differ;

wherein when gas flows into the inlet port, part of the gas goes into the first branch and part of the gas goes into the second branch;

wherein the first transducer device and the second transducer device are coupled to the main conduit device such that the main conduit device lies between the first and the second transducer devices and the main conduit device couples the first and second transducer devices together; and wherein the first and second locations are between the first and second transducer devices.

2. The apparatus of claim 1 wherein the inlet port is coupled substantially in the center of the inlet conduit.

3. The apparatus of claim 1 wherein the main conduit device is comprised of a first flange, a second flange, and a main conduit;

the main conduit has first and second ends, the first flange being connected to the main conduit at the first end, the second flange being connected to the main conduit at the second end;

and wherein the second end of the first branch is coupled to the first flange and the second end of the second branch is coupled to the second flange.

4. The apparatus of claim 3 wherein the first flange is connected to the first transducer device and the second flange is connected to the second transducer device.

5. The apparatus of claim 4 wherein the first transducer device is comprised of a first transducer and the second transducer device is comprised of a second transducer.

6. The apparatus of claim 5 wherein the first transducer device seals off the first end of the main conduit and the second transducer device seals off the second end of the main conduit.

7. The apparatus of claim 1 wherein the first and second branches of the inlet conduit together form a U-shape.

8. The apparatus of claim 1 wherein the first end of the first branch and the first end of the second branch are seamlessly connected together.

9. The apparatus of claim 1 wherein the third location is between the first and second transducer devices.

10. The apparatus of claim 9 wherein the third location is between the first and second locations.

11. An apparatus comprised of:

a first transducer having a surface;

a second transducer having a surface;

means for creating a first gas flow pattern near the first transducer;

means for creating a second gas flow pattern near the second transducer;

a device for causing the first transducer to send a signal to the second transducer and for measuring the time taken for the signal to travel from first transducer to the second transducer;

wherein the first gas flow pattern viewed by looking out from the surface of the first transducer is substantially the same as the second gas flow pattern viewed by looking out from the surface of the second transducer.

12. The apparatus of claim 11 further comprised of:

a main conduit device having first and second ends;

the first transducer located at the first end of the main conduit; and, the second transducer located at the second end of the main conduit.

13. The apparatus of claim 12 further comprised of:

an inlet conduit comprised of:

a first branch having a first end and a second end; and a second branch having a first end and a second end;

wherein the second end of the first branch is coupled to the first end of the main conduit device and the second end of the second branch is coupled to the second end of the main conduit device.

* * * * *